United States Patent
Baunach et al.

(10) Patent No.: US 8,337,684 B2
(45) Date of Patent: Dec. 25, 2012

(54) METHOD FOR OPERATING AN EXHAUST GAS SENSOR AND DEVICE FOR CARRYING OUT THE METHOD

(75) Inventors: Thorsten Baunach, Ammerbuch (DE); Martin Buchholz, Bietigheim-Bissingen (DE); Anna Karoline Winkler, Stuttgart-Feuerbach (DE); Jochen Domscheit, legal representative, Stuttgart (DE); Lothar Diehl, Gerlingen (DE)

(73) Assignee: Robert Bosch GmbH, Stuttgart (DE)

( * ) Notice: Subject to any disclaimer, the term of this patent is extended or adjusted under 35 U.S.C. 154(b) by 465 days.

(21) Appl. No.: 12/569,998

(22) Filed: Sep. 30, 2009

(65) Prior Publication Data

US 2010/0077836 A1   Apr. 1, 2010

(30) Foreign Application Priority Data

Sep. 30, 2008   (DE) .......................... 10 2008 042 505

(51) Int. Cl.
*G01N 27/419* (2006.01)
*G01N 27/407* (2006.01)

(52) U.S. Cl. ...................................... 204/425; 204/426

(58) Field of Classification Search .................. 204/425, 204/426, 427
See application file for complete search history.

(56) References Cited

U.S. PATENT DOCUMENTS

| | | | | |
|---|---|---|---|---|
| 4,702,816 A | * | 10/1987 | Hashimoto et al. | ........... 204/406 |
| 5,172,678 A | * | 12/1992 | Suzuki | ........... 123/688 |
| 5,340,462 A | * | 8/1994 | Suzuki | ........... 204/425 |
| 6,266,993 B1 | * | 7/2001 | Diehl et al. | ........... 73/1.06 |
| 6,656,337 B2 | * | 12/2003 | Kurokawa et al. | ........... 204/425 |
| 6,716,326 B2 | | 4/2004 | Steinlechner et al. | |
| 6,767,442 B1 | | 7/2004 | Scheer et al. | |
| 7,109,721 B2 | | 9/2006 | Maurer et al. | |
| 2002/0011410 A1 | * | 1/2002 | Inoue et al. | ........... 204/426 |
| 2002/0100698 A1 | * | 8/2002 | Detwiler et al. | ........... 205/784.5 |
| 2005/0029096 A1 | * | 2/2005 | Maurer et al. | ........... 204/402 |
| 2009/0116534 A1 | * | 5/2009 | Tabery et al. | ........... 374/45 |
| 2009/0308135 A1 | * | 12/2009 | Reinshagen et al. | ........... 73/23.2 |

FOREIGN PATENT DOCUMENTS

| | | |
|---|---|---|
| DE | 199 41 051 | 3/2001 |
| DE | 199 60 731 | 6/2001 |
| DE | 102 60 720 | 7/2004 |
| DE | 103 31 158 | 8/2005 |

\* cited by examiner

*Primary Examiner* — Lisa Caputo
*Assistant Examiner* — Punam Roy
(74) *Attorney, Agent, or Firm* — Merchant & Gould P.C.

(57) ABSTRACT

A method for operating an exhaust gas sensor, which has at least two electrodes, between which a pump current flows and between which a pump voltage occurs, said sensor being operated with a nominal operating temperature and a low temperature operation being intermittently provided at said sensor, wherein the temperature of the exhaust gas sensor is less with respect to the nominal operating temperature, and a device for carrying out the method are proposed. Provision is made according to the invention for the pump voltage to be acquired and for the low temperature operation to be influenced by the pump voltage.

9 Claims, 1 Drawing Sheet

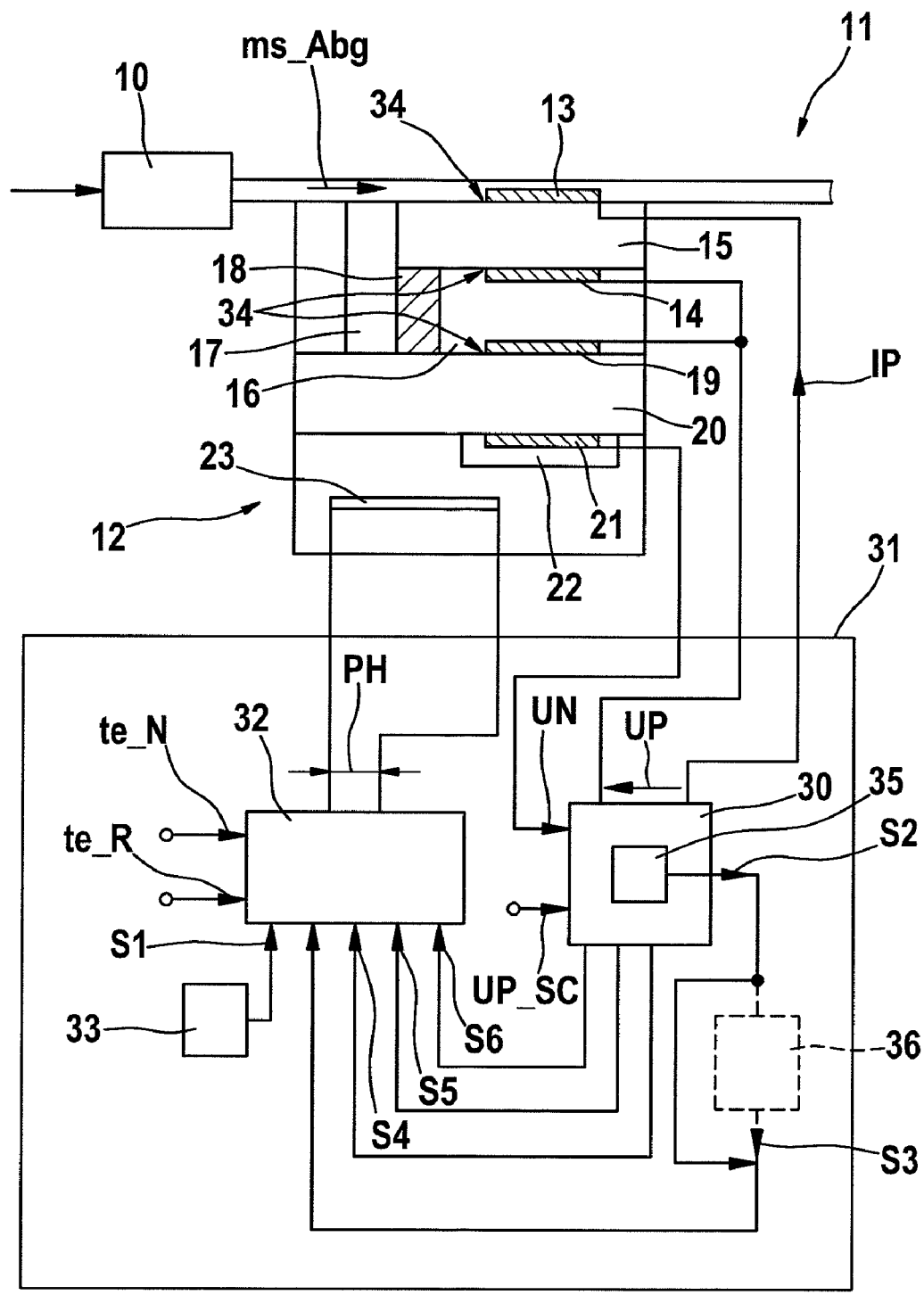

METHOD FOR OPERATING AN EXHAUST GAS SENSOR AND DEVICE FOR CARRYING OUT THE METHOD

This application claims benefit of Serial No. 10 2008 042 505.2, filed 30 Sep. 2008 in Germany and which application is incorporated herein by reference. To the extent appropriate, a claim of priority is made to the above disclosed application.

TECHNICAL FIELD

The invention is based on a method for operating an exhaust gas sensor, which is particularly provided for arrangement in the exhaust gas of an internal combustion engine, and on a device for carrying out the method according to the class of the independent claims.

A control unit program as well as a control unit program product is also the subject matter of the present invention.

BACKGROUND

In the German patent DE 102 60 720 A1, a method for operating a lambda sensor is described, which is intermittently operated with a reduced setback operating temperature, whereat a thermodynamic equilibrium can be set in the region of the electrodes. The at least intermittent operation of the lambda sensor with the setback operating temperature changes the cross sensitivity of the lambda sensor with respect to the cross sensitivity at the nominal operating temperature. This effect can be utilized to develop or suppress cross sensitivities of the lambda sensor in certain operating situations of the internal combustion engine, in whose exhaust gas channel the lambda sensor can be disposed. The CH4-cross sensitivity of the lambda sensor can, for example, be reduced with the setback operating temperature if the internal combustion engine is temporarily operated with a rich air/fuel mixture within the scope of the regeneration of a NOx storage catalytic converter. The setback operating temperature is specified by means of an intervention into the control circuit of the sensor heating device.

In the German patent DE 103 31 158 A1, a method for operating a lambda sensor is described, whose electrodes are intermittently impinged with an externally impressed regeneration current. It has been proven on the basis of experiments that a cleaning effect on the electrodes of the lambda sensor can thereby be achieved, which contributes to an extension of the time in service of the lambda sensor.

In the German patent DE 199 41 051 A1, a wideband lambda sensor is described, which has a sensor chamber, which is connected to a gas chamber via a diffusion barrier. An inner pump electrode is disposed in the sensor chamber. Said electrode together with an outer pump electrode and an electrolyte, which lies between the pump electrodes and conducts oxygen ions, comprises a pump cell. Oxygen ions can be pumped via the electrolyte out of the sensor chamber or into the sensor chamber with the pump cell. Beside the pump cell, a measuring cell is present, which lies between the inner pump electrode and the reference gas electrode, an electrolyte, which conducts oxygen ions, being likewise disposed between the inner pump electrode and the reference gas electrode. The measuring cell corresponds to a Nernst cell, whereat the potential difference developing in the thermodynamic equilibrium between the inner pump electrode and the reference electrode is proportional to the logarithm of the ratio of the partial pressure of the gas being tested in the sensor chamber and the partial pressure of the gas being tested in the air reference. The aim of a measurement of the exhaust gas lambda is to influence the oxygen partial pressure in the sensor chamber in such a way that the Nernst potential constantly remains at a specified value, which preferably corresponds to Lambda=1. A circuit arrangement makes sure that a pump current can flow. The polarity and the absolute value of the pump current depend on which value the specified Nernst potential has exceeded or undershot. The pump current which arises is a measurement for the exhaust gas lambda.

The German patent DE 199 60 731 A1 describes a NOx sensor which contains at least some components, whose operating modes are identical to the corresponding components of a lambda sensor.

The task underlying the invention is to state a method for operating an exhaust gas sensor, which is preferably provided for arrangement in the exhaust gas of an internal combustion engine, and a device for carrying out the method. Said method and device are thus provided to increase the reliability of the sensor signal of the exhaust gas sensor.

SUMMARY

The procedural approach according to the invention for operating an exhaust gas sensor, which has at least two electrodes, between which a pump current can flow and a pump voltage can occur, and which is normally operated with a nominal operating temperature, assumes that a low temperature operation is intermittently provided, wherein the temperature of the exhaust gas sensor is less with respect to the nominal operating temperature. Provision is made according to the invention for the pump voltage at the electrodes to be acquired and for the low temperature operation to be influenced by the acquired pump voltage.

The greater elevated pump voltage lying at the electrodes within the scope of the lower temperature operation raises the activity of the electrodes, which, for example, contain (platinum) grains. A conversion of the morphology of the electrodes takes place. A regeneration of the electrode surface results from the redistribution of the electrode grains. Furthermore, in particular a cleaning of the three-phase boundaries, wherein in each case the exhaust gas to be tested, the electrode grains and the sensor ceramic border on each other, is connected with said regeneration. As a result the oxygen ions are more easily integrated into the sensor ceramic. The procedural approach according to the invention allows for a cleaning of the exhaust gas sensor, respectively a regeneration, which makes sure that the characteristic curve of the exhaust gas sensor—the relation, for example, between the pump current and the air ratio lambda or between the pump current and the NOx concentration—remains at least approximately constant across the entire service life of the exhaust gas sensor.

The elevated pump voltage can basically be specified by an externally impressed voltage. Within the scope of the present application, another path is struck as a result of the sensor being operated at least intermittently within the scope of a low temperature operation, wherein the operating temperature of the exhaust gas sensor is less than the nominal operating temperature. The nominal operating temperature amounts, for example, to 780+/−30EC, the temperature of the lambda sensor, which is designated below as the regeneration temperature, in the lower temperature operation being less with respect to said nominal operating temperature. Provided that a regeneration temperature set point value is specified, a temperature can be specified, which is less with respect to the nominal operating temperature by 50-100EC.

At the lower operating temperature of the exhaust gas sensor, the pump voltage between the two electrodes increases at the same pump current due to the reduced mobility of the oxygen ions. An increase in the voltage at the electrodes of the exhaust gas sensor thereby results in the low temperature operation, which leads to the previously described increase in the activity of the electrodes. The low temperature operation can be specified during the start of operation of the exhaust gas sensor, whereat the exhaust gas sensor is to be initially heated up to the regeneration temperature and only subsequently to the nominal operating temperature, as well as based on the nominal operating temperature, i.e. within the scope of a reduction in the heating capacity of the exhaust gas sensor.

Provision is made in one configuration for the low temperature operation to be closed when a pump voltage threshold value is achieved. The time duration, during which the low temperature operation prevails, depends in this configuration on the starting temperature, whereat the low temperature operation was initiated, and the ambient conditions to which the exhaust gas sensor is exposed. A duration of the low temperature operation for a few seconds is achieved with this configuration.

Provision is made according to another configuration for the low temperature operation to be maintained for a specified time duration when a pump voltage threshold value is achieved. It can thereby be assured that the low temperature operation prevails for at least the specified time duration, which, for example, is established for a range of 5 to 30 seconds.

Provision is made in a modification of this configuration for the regeneration temperature set point value to be set during a specified time period. An additional change in the pump voltage is accepted here during the time duration.

Provision is made in another advantageous modification of this configuration for a pump voltage set point value, for example the pump voltage threshold value, to be set during the specified time duration; and in so doing, a change in the regeneration temperature can occur. A further increase in the pump voltage is thereby avoided. The effect of the low temperature operation can be limited with this measure. A regenerative effect is of course achieved with this low temperature operation; however, it can also lead to a damaging of the exhaust gas sensor over the long term.

Provision is made in another configuration for the low temperature operation to be enabled in a certain lambda range, which preferably lies between Lambda=1 to Lambda=2. The low temperature operation is thereby only enabled if an oxygen surplus exists in terms of the stoichiometry in the exhaust gas; and in so doing, the lower limit is to be established at stoichiometry, Lambda=1 and the upper limit at, for example, an oxygen concentration corresponding to Lambda=2. A pump current thereby occurs, at which an oxygen ion transport takes place from a measuring gas chamber of the exhaust gas sensor to an electrode arranged outside of the measuring gas chamber, said transport supporting the regeneration process of the electrode arranged in the measuring gas chamber.

The device according to the invention for carrying out the method first of all relates to a specially customized control unit, which contains means for carrying out the method.

The control unit contains in particular a heating control for the open-loop control, respectively closed-loop control, of the temperature of the exhaust gas sensor as well as means for acquiring the pump voltage, which corresponds to that voltage lying at the electrodes.

The control unit preferably contains at least one electrical storage, wherein the procedural steps are deposited as the control unit program.

Provision is made in the control unit program according to the invention for all steps of the method according to the invention to be executed if said program is run in a control unit.

The control unit program product according to the invention with a program code stored on a machine-readable carrier executes the method according to the invention if the program runs in a control unit.

Examples of embodiment of the invention are depicted in the drawing and explained in detail in the following description.

BRIEF DESCRIPTION OF THE FIGURES

FIG. 1 shows a technical environment, wherein a method according to the invention runs.

DETAILED DESCRIPTION

The FIGURE shows an internal combustion engine 10, in whose exhaust gas region 11 an exhaust gas mass flow ms_Abg occurs, which impinges an exhaust gas sensor 12. A wideband lambda sensor 12 is assumed in the depicted example of embodiment, which, for example, is described in the German patent DE 199 41 051 A1. The exhaust gas sensor 12 can also be implemented as a NOx sensor 12 according to the German patent DE 199 60 731 A1, which was likewise cited at the beginning of the application.

The exhaust gas sensor 12 contains a first and second electrode 13, 14, which are separated by a sensor ceramic 15, the first electrode 13 being exposed to the exhaust gas mass flow ms_Abg. The second electrode 14 is arranged in a measuring gas chamber 16. A portion of the exhaust gas can flow into said chamber 16 via an air supply duct 17 and a diffusion barrier 18. A third electrode 19, which is electroconductively connected to the second electrode 14 and is connected to a fourth electrode 21 disposed in a reference gas canal 22 via a sensor ceramic 20, is in the measuring gas chamber 16. Provision is made for a sensor heater 23 for heating the exhaust gas sensor 12.

The example of embodiment assumes, as previously noted, a wideband lambda sensor 12, which aims to set an air ratio Lambda=1 in the measuring gas chamber 16. The Nernst voltage UN occurring between the third and fourth electrode 19, 21, which lies at approximately 450 mV when it is assumed that a stoichiometric mixture is present in the measuring gas chamber 16 and ambient air is present in the reference gas channel 22, is used as the actual variable for a control loop. An oxygen concentration deviating from a stoichiometric mixture in the measuring gas chamber 16 is counteracted by the application of a pump voltage UP between the first and second electrode 13, 14 and a transport of oxygen ions in the sensor ceramic 15, which was made possible by said application. When an oxygen excess occurs, an oxygen ion transport occurs from the measuring gas chamber 16 to the exhaust gas region 11. When an oxygen defict occurs, an oxygen ion transport takes place from the exhaust gas region 11 into the measuring gas chamber 16. The oxygen ion transport is set into motion by the application of the pump voltage UP to the first and second electrode 13, 14 so that a pump current IP results, which in the case of an oxygen excess in the measuring gas chamber 16 is to be defined as positive and in the case of an oxygen deficit in the measuring gas chamber 16 is to be accordingly defined as negative. When stoichiometry occurs in the measuring gas chamber 16, a zero crossing of the pump current IP results.

Provision is made for an exhaust gas sensor operating arrangement 30 for operating the exhaust gas sensor 12, which is to be disposed in a control unit 31. The Nernst voltage UN is provided to the exhaust gas sensor operating arrangement 30 as an input variable. The exhaust gas sensor operating arrangement 30 establishes the pump current IP as a function of deviations of the set point value for the Nernst voltage UN. In practice the first electrode 13 is connected to a voltage source via a current limiting resistor, which is trimmable if need be, so that a pump current IP can result and the pump voltage UP at the first electrode 13 can simultaneously change as a function of the internal resistance of the sensor ceramic 15 between the two electrodes 13, 14. The pump voltage UP of the exhaust gas sensor arrangement 30 occurring at the first electrode 13 as well as the pump current IP, which is for example a measure for the air ratio lambda or the NOx concentration in the exhaust gas mass flow ms_Abg, can thereby be acquired.

The sensor heating device 23 is provided for the creation of the operational readiness of the exhaust gas sensor 12. Said heating device 23 is provided in particular for the heating up of the sensor ceramic 15, 20 so that the sensor ceramic 15, 20 can conduct oxygen ions in sufficient quantity. A heat output PH, which is supplied by a heater control 32 is provided to the sensor heating device 23. The closed-loop control takes place during the normal operation of the exhaust gas sensor 12 at a nominal operating temperature te_N, which is provided as a set point value to the heater control 32. In so doing, the sensor heating device 23 can be adjusted to the set point value. The temperature actual value can then be ascertained on the basis of an acquisition of the internal resistance of the sensor heating device 23. It is, however, alternatively possible to ascertain the temperature actual value from the electrical relationships either between the first and second electrode 13, 14 or the third and fourth electrode 19, 21. The nominal operating temperature amounts to, for example, 780EC+/−30EC.

Using a switch signal S1, an exhaust gas sensor regeneration open-loop control 33 can cause the heater control 32 to reduce the temperature with respect to the nominal operating temperature te_N. The regeneration temperature can be established at the regeneration temperature set point value te_R, which, for example, lies at 50-100EC below the nominal operating temperature te_N. The regeneration temperature must, however, not be specified. The regeneration temperature, which constantly drops during the entire low temperature operation or if need be adjusts to a fluctuating value, can arise as a function of the operating procedure. The regeneration temperature lies, however, in each case below the nominal operating temperature te_N. The regeneration temperature can, for example, be set already during the heating-up process of the exhaust gas sensor 12 after the startup procedure so that the exhaust gas sensor 12 is initially operated for some time with the regeneration temperature set point value te_R before adjustment to the nominal operating temperature te_N. The regeneration temperature is, however, preferably achieved by a lowering of the temperature away from the nominal operating temperature te_N.

As a result of operating the exhaust gas sensor 12 with the regeneration temperature, the internal resistance between the two electrodes 13, 14 increases due to the reduced oxygen ion conductivity of the sensor ceramic 15 so that the pump voltage UP rises at the first electrode 13 starting from a value of, for example, 0-600 mV to higher values up to, for example, 1-2 V.

The elevated pump voltage UP leads to an increased activity of the material of the electrodes 13, 14 and the material of the third electrode 19, which is electrically connected to the electrode 14. In so doing, the morphology of the electrodes 13, 14, 19 changes. This change brings about a cleaning of the electrodes 13, 14, 19, in particular of the second and third electrode 14, 19, which are not exposed to the exhaust gas mass flow ms_Abg. A cleaning effect particularly occurs at the three-phase boundaries 34, which are present between the exhaust gas, the first electrode 13 and the sensor ceramic 15, respectively between the measuring gas chamber 16, the second/third electrode 14, 19 and the sensor ceramic 15. Due to the concrete implementation of the electrodes 13, 14, 19, numerous three-phase boundaries are in each case present in the region of the electrodes 13, 14, 19, not only on the edge of the electrodes 13, 14, 19 as shown in the example of embodiment.

The cleaning effect consists of deposits, for example oil incineration ash, diffusing into the sensor ceramic 15 in the region of the three-phase boundaries due to the change in the morphology of the electrodes 13, 14, 19. The effect is then that the three-phase boundaries, which are essential for the functioning of the exhaust gas sensor, are regenerated. The characteristics of the sensor ceramic 15 are indeed compromised by the diffusion of foreign particles into the sensor ceramic 15; however, it has been shown that with the measure according to the invention, the characteristic curve of the exhaust gas sensor 12 can be at least approximately constantly maintained over its entire service life.

The regeneration open-loop control 33 begins the regeneration with the first switch signal S1, which continuously allocates the regeneration open-loop control 33, for example in each case after 30 to 60 minutes of operation of the exhaust gas sensor 12. After that the heater control 32 reduces the heat output PH or preferably completely switches the heating device 23 off. In so doing, the temperature of the exhaust gas sensor 12 drops starting from the nominal operating temperature te_N to the regeneration temperature. In this low temperature operation, the regeneration temperature is a constantly decreasing temperature, which lies below the nominal operating temperature te_N.

Provision is made according to one configuration for the low temperature operation to close if the pump voltage UP has achieved a pump voltage threshold value UP_SC, which, for example, is established at a voltage of 1.0 V to 2 V. The exhaust gas sensor operating arrangement 30 contains a comparator 35, which compares the pump voltage UP with the pump voltage threshold value UP_SC and provides a second switch signal S2 when the two values correlate, respectively when said threshold value UP_SC is exceeded. Said switch signal S2 is supplied to the heater control, which then closes the low temperature operation and again specifies the nominal operating temperature te_N. The thereby attainable low temperature operation is limited to a few seconds.

A timer 36, which is activated by the second switch signal S2, is plotted with dashed lines in the signal pathway of the second switch signal S2. Provision can be made according to a particularly advantageous configuration for the low temperature operation to still be maintained after achieving the pump voltage threshold value UP_SC for the time specified by the timer 36, for example 5 seconds to 30 seconds. In so doing, the low temperature operation can at least be approximately maintained for a certain time, only the time being variable at which the pump voltage threshold value UP_SC is achieved. After the time specified by the timer 36 has elapsed, the timer 36 releases a third switch signal S3 to the heater control 32, which then closes the low temperature operation and again specifies the nominal operating temperature te_N.

During the time duration specified by the timer 36, provision can be made for at least two different procedural approaches:

Provision is made according to a first example of embodiment for the low temperature operation to be controlled in a closed loop as a function of a measurement for the pump voltage UP so that the increased pump voltage UP remains at least approximately constant during the time duration. This closed-loop control can occur in the simplest case within the scope of an on-off control, the exhaust gas sensor operating arrangement 30 releasing a fourth switch signal S4 to the heater control 32. In this case, the increased pump voltage UP remains at least approximately constant, the regeneration temperature, however, being able to fluctuate.

Provision is made according to another example of embodiment for the temperature to be adjusted within the scope of the low temperature operation to the regeneration temperature set point value ti_R during the specified time. In so doing, such a regeneration temperature set point value ti_R is fixedly specified and is established, for example, at a value of 50-100EC below the nominal operating temperature te_N. In the example of embodiment shown, it is assumed that this operation is also actuated by the exhaust gas sensor operating arrangement 30, the exhaust gas sensor operating arrangement 30 providing a fifth switch signal S5 to the heater control 32. In this case, the temperature of the exhaust gas sensor 12 is at least approximately adjusted to the regeneration temperature set point te_N. In so doing, a further increase in the elevated pump voltage UP, which occurs as the case may be, must, however, be accepted.

Provision can be made according to one configuration for the low temperature operation to only then be specified if the exhaust gas lambda lies in a range of, for example, Lambda=1 to Lambda=2. For this purpose, the exhaust gas sensor operating arrangement 30 provides the sixth switch signal 6 to the heater control 32 so that the heater control 32 implements the low temperature operation only when the sixth switch signal S6 occurs. The implementation of the low temperature operation at a lean exhaust gas lambda particularly allows for a reliable regeneration of the second/third electrode 14, 19, which is arranged in the measuring gas chamber 16. This is the case because when the exhaust gas lambda is lean, the oxygen ion flow runs from the second electrode 14 to the first electrode 13 so that a diffusing of undesirable surface contaminants into the sensor ceramic 15 is supported.

In the examples of embodiment, it is assumed in each case that the second, third, fourth, fifth and sixth switch signal S2, S3, S4, S5, S6 are supplied to the temperature control 32. In principle it is, however, possible to also provide these signals to the exhaust gas sensor regeneration open-loop control 33, which repeatedly specifies the low temperature operation, for example, in a time period of 15 minutes to 90 minutes, by providing the first switch signal S1.

The invention claimed is:

1. A method of operating an exhaust gas sensor comprising at least two electrodes between which a pump current flows and a pump voltage occurs, the method comprising:
    operating the sensor at a nominal operating temperature;
    intermittently switching operation of the sensor to a low temperature operation in which the temperature of the exhaust gas sensor is less than the nominal operating temperature;
    acquiring the pump voltage, wherein the low temperature operation is influenced by the pump voltage; and
    discontinuing the low temperature operation when a pump voltage threshold value is achieved.

2. The method of claim 1, further comprising setting a measurement for a pump voltage set point value by influencing the temperature of the exhaust gas sensor after the pump voltage threshold value has been achieved.

3. The method of claim 2, further comprising setting the pump voltage threshold value to be the pump voltage set point value.

4. The method of claim 1, further comprising regulating the temperature of the exhaust gas sensor at a specified regeneration temperature set point.

5. The method of claim 1, further comprising enabling the low temperature operation in a lambda range of the exhaust gas of at least approximately between Lambda=1 to Lambda=2.

6. A device comprising at least one customized control unit configured to operate an exhaust gas sensor comprising at least two electrodes between which a pump current flows and a pump voltage occurs, the control unit configured to: operate the sensor at a nominal operating temperature; intermittently switching operation of the sensor to a low temperature operation in which the temperature of the exhaust gas sensor is less than the nominal operating temperature; acquire the pump voltage, wherein the low temperature operation is influenced by the pump voltage; and maintain the low temperature operation for a time duration when a pump voltage threshold value is achieved.

7. The device according of claim 6, wherein the at least one control unit includes a heater control that adjusts the nominal operating temperature of the exhaust gas sensor and a regeneration set point value of the low temperature operation.

8. A non-transitory computer-readable storage medium comprising instructions that, when executed by a control unit of an electronic computing system, causes the control unit to execute a method of operating an exhaust gas sensor comprising at least two electrodes between which a pump current flows and a pump voltage occurs, the method comprising: operating the sensor at a nominal operating temperature; intermittently switching operation of the sensor to a low temperature operation in which the temperature of the exhaust gas sensor is less than the nominal operating temperature; acquiring the pump voltage, wherein the low temperature operation is influenced by the pump voltage; and discontinuing the low temperature operation when a pump voltage threshold value is achieved.

9. A control unit program product with a program code that is stored on a non-transitory machine-readable carrier to implement that, when executed in a control unit, a method of operating an exhaust gas sensor comprising at least two electrodes between which a pump current flows and a pump voltage occurs, the method comprising: operating the sensor at a nominal operating temperature; intermittently switching operation of the sensor to a low temperature operation in which the temperature of the exhaust gas sensor is less than the nominal operating temperature; acquiring the pump voltage, wherein the low temperature operation is influenced by the pump voltage; and discontinuing the low temperature operation when a pump voltage threshold value is achieved.

* * * * *

UNITED STATES PATENT AND TRADEMARK OFFICE
CERTIFICATE OF CORRECTION

PATENT NO. : 8,337,684 B2  
APPLICATION NO. : 12/569998  
DATED : December 25, 2012  
INVENTOR(S) : Baunach et al.

Page 1 of 1

It is certified that error appears in the above-identified patent and that said Letters Patent is hereby corrected as shown below:

In the Claims:

Col. 8, line 25, claim 6: "switching operation of the" should read --switch operation of the--

Signed and Sealed this
Sixteenth Day of July, 2013

Teresa Stanek Rea
*Acting Director of the United States Patent and Trademark Office*